United States Patent [19]

Lesher et al.

[11] Patent Number: 4,512,993

[45] Date of Patent: Apr. 23, 1985

[54] 4(OR 5)-(PYRIDINYL)-2-PYRIMIDINAMINES AND CARDIOTONIC USE THEREOF

[75] Inventors: George Y. Lesher, Schodack; Baldev Singh, East Greenbush, both of N.Y.

[73] Assignee: Sterling Drug Inc., New York, N.Y.

[21] Appl. No.: 516,820

[22] Filed: Jul. 25, 1983

[51] Int. Cl.$^3$ .................. A61K 31/505; C07D 239/24
[52] U.S. Cl. ..................................... 514/275; 544/331
[58] Field of Search ........................ 544/331; 424/251

[56] References Cited

U.S. PATENT DOCUMENTS

| | | | |
|---|---|---|---|
| Re. 30,024 | 6/1979 | Lesher et al. ........................ | 544/319 |
| 4,086,233 | 4/1978 | Lesher et al. ........................ | 546/257 |
| 4,118,571 | 10/1978 | Lesher et al. ........................ | 544/319 |

OTHER PUBLICATIONS

Bennett et al., Journal Medicinal Chemistry, 1978, vol. 21, No. 7, pp. 623–628.

*Primary Examiner*—Mark L. Berch
*Assistant Examiner*—Cecilia Shen
*Attorney, Agent, or Firm*—Robert K. Bair; B. Woodrow Wyatt; Paul E. Dupont

[57] ABSTRACT

Shown are 2-(NB)-4-PY-5-Q-pyrimidines (I) and 2-(NB′)-5-PY-4-Q′-pyrimidines (II) or salts thereof, where PY is 4- or 3-pyridinyl or 4- or 3-pyridinyl having one or two lower-alkyl substituents, Q and Q′ are each hydrogen or methyl, NB is dimethylamino or N-(2-hydroxyethyl)methylamino and NB′ is amino, dimethylamino, acetylamino or propionylamino; the preparation thereof; and, their cardiotonic use.

8 Claims, No Drawings

4(OR 5)-(PYRIDINYL)-2-PYRIMIDINAMINES AND CARDIOTONIC USE THEREOF

BACKGROUND OF THE INVENTION (a) Field of the Invention

This invention relates to 4(or 5)-(pyridinyl)-2-pyrimidinamines and their cardiotonic use.

(b) Information Disclosure Statement 4-(4-Pyridinyl)-2-pyrimidinamine (no. 4a) and N-methyl-4-(4-pyridinyl)-2-pyrimidinamine (no. 4g) were reported by Bennett et al. [J. Med. Chem. 21, 623–628 (1978)] to be active when tested for antiinflammatory activity against carrageenan-induced edema in the rat but were said to be inactive when tested against adjuvant-induced edema in the rat. Other compounds reported active against carrageenan-induced edema were 4-(3-pyridinyl)-2-pyrimidinamine (4e), 5-methyl-4-(4-pyridinyl)-2-pyrimidinamine (4p), as well as the N-acetyl and N-propionyl derivatives (4h and 4i) of 4-(4-pyridinyl)-2-pyrimidinamine. Discussion of the antiinflammatory activity of the compounds disclosed in this publication concluded as follows:

"None of the compounds tested against adjuvant-induced edema in the rat displayed a level of activity sufficient to warrant further investigation. Based on additional testing it would appear that these compounds represent a series of false positives in the carageenan-induced edema model."

Compounds 4a and 4g of Bennett et al. were prepared by reacting 3-dimethylamino-1-(4-pyridinyl)-2-propen-1-one with guanidine or 1-methylguanidine, respectively. Compound 4e was prepared by reacting 3-dimethylamino-1-(3-pyridinyl)-2-propen-1-one with guanidine and compound 4p was prepared by reacting 3-dimethylamino-2-methyl-1-(4-pyridinyl)-2-propen-1-one with guanidine.

Isomeric 2-(4- or 3-pyridinyl)-4-pyrimidinamines are shown as anti-allergic agents in the Lesher and Singh U.S. Pat. No. 4,086,233, issued Apr. 25, 1978, and U.S. Pat. No. Re. 30,024, reissued June 5, 1979, of U.S. Pat. No. 4,032,523, issued June 28, 1977.

N-Acetyl-2-(4-pyridinyl)-4-pyrimidinamine and other N-alkanoyl compounds are shown as intermediates in the Lesher and Singh U.S. Pat. No. 4,118,571, issued Oct. 3, 1978.

SUMMARY OF THE INVENTION

In a composition of matter aspect, the invention resides in 4-PY-5-Q-2-pyrimidinamine or 5-PY-4-Q'-2-pyrimidinamine having the formula I or II respectively

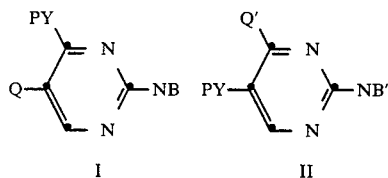

I        II or acid-addition salt thereof, where PY is 4- or 3-pyridinyl or 4- or 3-pyridinyl having one or two lower-alkyl substituents, Q and Q' are each hydrogen or methyl, NB is dimethylamino or N-(2-hydroxyethyl)methylamino and NB' is amino, dimethylamino, acetylamino or propionylamino. The compounds of formulas I and II are useful as cardiotonic agents, as determined by standard pharmacological evaluation procedures.

A composition aspect of the invention resides in the cardiotonic composition for increasing cardiac contractility, said composition comprising a pharmaceutically acceptable inert carrier and, as the active component thereof, a cardiotonically effective amount of 4-PY-5-Q-2-pyrimidinamine and formula I or 5-PY-4-Q'-2-pyrimidinamine of formula II, where PY, Q, Q', NB and NB' are defined as in formula I or II, or pharmaceutically acceptable acid-addition salt thereof.

In a method aspect, the invention resides in the method for increasing cardiac contractility in a patient requiring such treatment which comprises administering orally or parenterally in a solid or liquid dosage form to such patient a cardiotonically effective amount of 4-PY-5-Q-2-pyrimidinamine of formula I or 5-PY-4-Q'-2-pyrimidinamine of formula II, where PY, Q, Q', NB and NB' are defined as in formula I or II, or pharmaceutically acceptable acid-addition salt thereof.

DETAILED DESCRIPTION INCLUSIVE OF PREFERRED EMBODIMENTS

Preferred embodiments are those of formula I or II where PY is 4-pyridinyl or 3-pyridinyl, Q is hydrogen, Q' is methyl, NB is as defined above and NB' is amino.

The term "lower-alkyl" as used herein, e.g., as a substituent for PY, means alkyl radicals having from one to four carbon atoms which can be arranged as straight or branched chains, illustrated by methyl, ethyl, n-propyl, isopropyl, n-butyl, 2-butyl and isobutyl.

The symbol "PY" as used herein, e.g., as the 4-substituent in the pyrimidine ring of the compounds having formula I or the 5-substituent in the pyrimidine ring of the compounds having formula II, means 4- or 3-pyridinyl or 4- or 3-pyridinyl having one or two lower-alkyl substituents, illustrated by 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diethyl-3-pyridinyl, 2,6-diisopropyl-4-pyridinyl, and the like.

The compounds of the invention having formula I or II are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salt include preferably those which produce, when combined with the free base, pharmaceutically acceptable salts, that is, salts whose anions are relatively innocuous to the animal organism in pharmaceutical doses of the salts, so that the beneficial cardiotonic properties inherent in the free base of the cardiotonically active compounds of the invention are not vitiated by side effects ascribable to the anions. In practicing the invention, it is convenient to use the free base form or the hydrochloric acid-addition salt; however, appropriate pharmaceutically acceptable salts within the scope of the invention are those derived from mineral acids such as sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, which give the sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of the invention were assigned on the basis of evidence provided by infrared, nuclear magnetic resonance and mass spectra, by the correspondence of calculated and found values for the elementary analyses, and, by their method of preparation.

The manner of making and using the instant invention will now be generally described so as to enable a person skilled in the art of pharmaceutical chemistry to make and use the same, as follows.

The compounds of formula I were prepared by heating 1,1-dimethylguanidine or 1-methyl-1-(2-hydroxyethyl)-guanidine, preferably as its acid-addition salt, e.g., sulfate or carbonate, with 3-dimethylamino-2-Q-1-PY-2-propen-1-one. When the guanidine salt is derived from a strong acid, e.g., sulfuric or hydrochloric acid, the reaction is run in the presence of a base such as an alkali lower-alkoxide in a lower-alkanol, preferably sodium ethoxide or methoxide in refluxing ethanol or methanol. Although it can be used, no base is necessary using a guanidine salt of a weak acid, such as a carbonate or an acetate. Other solvents can be used, for example, n-propanol, 2-propanol, p-dioxane, tetrahydrofuran, dimethylformamide, 1,2-dimethoxyethane, and the like.

The intermediate 3-dimethylamino-2-Q-1-PY-2-propen-1-ones are generally known and are prepared by known means, for example, as described by Bennett et al. [J. Med. Chem. 21, 623–628 (1978)].

The compounds of formula II where NB' is amino or dimethylamino were prepared by heating guanidine or N,N-dimethylguanidine or salt thereof, e.g., sulfate or carbonate, with 3-dimethylamino-2-PY-3-Q'-2-propen-1-al. This reaction can be run as described above for the preparation of the compounds of formula I by reacting said guanidine or salt with 3-dimethylamino-3-Q-1-PY-2-propen-1-one.

The intermediate 3-dimethylamino-2-PY-3-Q'-2-propen-1-als are generally known and are prepared by known means (U.S. Pat. No. 4,004,012, issued Jan. 18, 1977).

The compounds of formula II where NB' is acetylamino or propionylamino are prepared by reacting the compound of formula II where NB' is amino with an acetylating or propionylating agent, preferably acetic or propionic anhydride, conveniently by heating the reactants in a suitable aprotic solvent, e.g., pyridine, p-dioxane, tetrahydrofuran, dimethylformamide, 1,2-dimethoxyethane, and the like.

The following examples will further illustrate the invention without, however, limiting it thereto.

A. 4-PY-5-Q-2-PYRIMIDINAMINES

A-1. N,N-Dimethyl-4-(3-pyridinyl)-2-pyrimidinamine— To a solution containing 2.3 g of sodium dissolved in 200 ml of ethanol was added 13.6 g of 1,1-dimethylguanidine sulfate and 17.6 g of 3-dimethylamino-1-(3-pyridinyl)-2-propen-1-one and the resulting mixture was refluxed for 3 hours and allowed to cool. The solid was filtered off and the filtrate was evaporated to dryness. The residue was taken up in isopropyl alcohol, the solution made acidic with acetic acid and filtered. The filtrate was evaporated to dryness and taken up in ether. The ether layer was treated with decolorizing charcoal, washed several times with 5% aqueous potassium bicarbonate solution and then treated with ethanolic hydrogen chloride, stirred well and the separated solid collected. The solid was recrystallized from a minimum quantity of hot methanol followed by addition of ethanol and cooling. The precipitated product was collected and dried to produce 9.2 g of N,N-dimethyl-4-(3-pyridinyl)-2-pyrimidinamine as its dihydrochloride, m.p. 230°–241° C.

A-2. N-(2-Hydroxyethyl)-N-methyl-4-(4-pyridinyl)-2-pyrimidinamine— To a solution containing 5 g of sodium dissolved in 300 ml of ethanol was added 20 g of N-(2-hydroxyethyl)-N-methylguanidine sulfate and 17.6 g of 3-dimethylamino-1-(4-pyridinyl)-2-propen-1-one and the mixture was heated with stirring on a steam bath for 75 minutes. The reaction mixture was made acidic with acetic acid, next made basic with ammonium hydroxide and the resulting solution was evaporated to dryness. The residue was extracted with ether and then with warm isopropyl acetate. The combined extracts were chilled and the separated solid was collected. The solid was dissolved in methylene dichloride, treated with decolorizing charcoal and filtered. The filtrate was evaporated to dryness, the residue dissolved in isopropyl alcohol, and the alcohol solution treated with excess hydrogen chloride in absolute ethanol. The separated solid was collected, washed successively with isopropyl alcohol, hot isopropyl acetate and ether, and dried to produce 22.5 g of N-(2-hydroxyethyl)-N-methyl-4-(4-pyridinyl)-2-pyrimidinamine as its dihydrochloride, m.p. 191°–195° C.

The above intermediate N-(2-hydroxyethyl)-N-methylguanidine sulfate was prepared as follows: A mixture containing 83.6 g of methyl isothiourea sulfate and 90 g of N-(2-hydroxyethyl)methylamine was heated on a steam bath under vacuum until no more methyl mercaptan was evolved. The solid remaining was boiled successively with hot isopropyl alcohol, hot absolute ethanol and then ether, and collected to yield 91 g of crystalline N-(2-hydroxyethyl)-N-methylguanidine sulfate.

A-3. N-(2-Hydroxyethyl)-N-methyl-4-(3-pyridinyl)-2-pyrimidinamine as its dihydrochloride hemihydrate, m.p. 201°–205° C., was prepared following the procedure described in Example A-2 using 5.5 g of sodium in 300 ml of absolute ethanol, 22 g of N-(2-hydroxyethyl-N-methylguanidine sulfate, 17.6 g of 3-dimethylamino-1-(3pyridinyl)-2-propen-1-one and a reflux period of 90 minutes.

A-4. N,N-Dimethyl-4-(4-pyridinyl)-2-pyrimidinamine—To 500 ml of absolute ethanol was added 26.4 g of 3-dimethylamino-1-(4-pyridinyl)-2-propen-1-one, 19.1 g of 1,1-dimethylquanidine sulfate and 7.6 g of sodium methoxide. The reaction mixture was refluxed for 3 hours, allowed to cool to room temperature and filtered. The filtrate was evaporated to remove most of the ethanol and was then treated with several volumes of ether. The resulting precipitate was filtered off and the filtrate concentrated in vacuo to yield 23.6 g of viscous orange oil. The oil was transferred to a silica gel bed (5 inches in diameter and 3 inches high) with the aid of 20 ml ether. The bed was eluted with ether and the ether fractions (all containing only one spot) were combined and evaporated to dryness. The remaining viscous oil, on chilling and scratching with a glass rod, crystallized. The solid was broken up, triturated with a small volume of anhydrous ether, collected and dried in a vacuum dessicator to remove last traces of solvent from the silica gel treatment to yield 16.3 g of hygroscopic N,N-dimethyl-4-(4-pyridinyl)-2-pyrimidinamine, m.p. 44–47 C.

Acid-addition salts of N,N-dimethyl-4-(4-pyridinyl)-2-pyrimidinamine are conveniently prepared by adding to a mixture of 1 g of N,N-dimethyl-4-(4-pyridinyl)-2-pyrimidinamine in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of N,N-dimethyl-4-(4-pyridinyl)-2-pyrimidinamine and the appropriate acid, e.g., lactic acid or hydrochloric acid, to prepare respectively the lactate or hydrochloride salt of N,N-dimethyl-4-(4-pyridinyl)-2-pyrimidinamine in aqueous solution.

A-5. N,N,5-Trimethyl-4-(4-pyridinyl)-2-pyrimidinamine, m.p. 114°–116° C., 9.5 g, was obtained following the procedure described in Example A-5 using 13.6 g of N,N-dimethyl guanidine sulfate, 20.9 g of 3-dimethylamino-2-methyl-1-(4-pyridinyl)-2-propen-1-one, 5.4 g of sodium methoxide, 380 ml of absolute ethanol and a reflux period of 17 hours.

Acid-addition salts of N,N,5-trimethyl-4-(4-pyridinyl)-2-pyrimidinamine are conveniently prepared by adding to a mixture of 1 g of N,N,5-trimethyl-4-(4-pyridinyl)-2-pyrimidinamine in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of N,N,5-trimethyl-4-(4-pyridinyl)-2-pyrimidineamine and the appropriate acid, e.g., lactic acid or hydrochloric acid, to prepare respectively the lactate or hydrochloride salt of N,N,5-trimethyl-4-(4-pyridinyl)-2-pyrimidinamine in aqueous solution.

Following the procedure of Example A-1 but using in place of 1,1-dimethylguanidine sulfate and 3-dimethylamino-1-(3-pyridinyl)-2-propen-1-one molar equivalent quantities of the appropriate guanidine derivative and 3-dimethylamino-2-Q-1-PY-2-propen-1-one, it is contemplated that the corresponding 4-PY-5-Q-2-pyrimidinamines of Examples A-6 through A-9 can be obtained.

A-6. N-(2-Hydroxyethyl)-N-methyl-4-(2-methyl-3-pyridinyl)-2-pyrimidinamine, using N-(2-hydroxyethyl)-N-methylguanidine sulfate and 3-dimethylamino-1-(2-methyl-3-pyridinyl)-2-propen-1-one.

A-7. N,N,5-Trimethyl-4-(5-methyl-3-pyridinyl)-2-primidinamine, using N,N-dimethylguanidine sulfate and 3-dimethylamino-2-methyl-1-(5-methyl-3-pyridinyl)-2-propen-1-one.

A-8. 4-(3-Ethyl-4-pyridinyl)-N,N-dimethyl-2-pyrimidinamine, using 1,1-dimethylguanidine sulfate and 1-(3-ethyl-4-pyridinyl)-3-dimethylamino-2-propen-1-one.

A-9. N,N-Dimethyl-4-(2,6-dimethyl-4-pyridinyl)-2-pyrimidinamine, using 1,1-dimethylguanidine sulfate and 3-dimethylamino-1-(2,6-dimethyl-4-pyridinyl)-2-propen-1-one.

B. 5-PY-4-Q'-2-PYRIMIDINAMINES

B-1. 5-(4-Pyridinyl)-2-pyrimidinamine—A mixture containing 20 g of 3-dimethylamino-2-(4-pyridinyl)-2-propen-1-al, 25 g of guanidine carbonate and 100 ml of ethanol was refluxed for 4 hours and concentrated in vacuo to remove the solvent. The residue was stirred in ice cold water and the crystalline product was collected, washed with water and dried to produce 12.1 g of 5-(4-pyridinyl)-2-pyrimidinamine, m.p. 210°–212° C.

Acid-addition salts of 5-(4-pyridinyl)-2-pyrimidinamine are conveniently prepared by adding to a mixture of 1 g of 5-(4-pyridinyl)-2-pyrimidinamine in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of 5-(4-pyridinyl)-2-pyrimidinamine and the appropriate acid, e.g., lactic acid or hydrochloric acid, to prepare respectively the lactate or hydrochloride salt of 5-(4-pyridinyl)-2-pyrimidinamine in aqueous solution.

B-2. N,N-Dimethyl-5-(4-pyridinyl)-2-pyrimidinamine, m.p. 176°–178° C., 5.8 g, was prepared following the procedure described in Example B-1 using 17.6 g of 3-dimethylamino-2-(4-pyridinyl)-2-propen-1-al, 27.2 g of 1,1-dimethylguanidine sulfate, 10.8 g of sodium methoxide, 100 ml of ethanol and recrystallization of the product from ethanol.

B-3. N,N-Dimethyl-5-(3-pyridinyl)-2-pyrimidinamine—A mixture containing 17 g of 3-dimethylamino-2-(3-pyridinyl)-2-propen-1-al, 13.6 g of 1,1-dimethylguanidine sulfate, 16 g of sodium methoxide and 500 ml of methanol was refluxed for 3 hours and then allowed to stand at room temperature overnight. The reaction mixture was evaporated in vacuo to remove the solvent and water was added to the residue. The solid was collected, washed with water and dried. The solid was dissolved in 6N hydrochloric acid, the solution filtered through diatomaceous earth and the filtrate treated with isopropyl alcohol and cooled. The separated product was collected, washed successively with isopropyl alcohol and ether, and dried to produce 4 g of N,N-dimethyl-5-(3-pyridinyl)-2-pyrimidamine as its hydrochloride, m.p. 295° C. with decomposition.

B-4. 4-Methyl-5-(4-pyridinyl)-2-pyrimidinamine—A mixture containing 15.6 g of 3-dimethylamino-3-methyl- 2-(4-pyridinyl)-2-propen-1-al, 17.7 g of guanidine carbonate, 5.4 g of sodium methoxide and 150 ml of absolute ethanol was stirred at room temperature for 6 hours and then heated on a steam bath for about 20 minutes and cooled. The reaction mixture was stripped in vacuo and the resulting solid residue was slurried with water, the mixture acidified using acetic acid and put in a refrigerator overnight. The separated solid was collected, dried in a vacuum oven at 60° C., recrystallized from hot ethanol and dried in vacuo at 95° C. to produce 9.6 g of 4-methyl-5(4-pyridinyl)-2-pyrimidinamine, m.p. 215°–217° C.

B-5. N-[5-(4-Pyridinyl)-2-pyrimidinyl]acetamide—A mixture containing 17.2 g of 5-(4-pyridinyl)-2-pyrimidamine, 61.2 g of acetic anhydride and 200 ml of pyridine was refluxed for 2 hours and cooled. The separated solid was collected, washed successively with ethanol and ether, and then dried. The solid was recrystallized from dimethylformamide, washed successively with ethanol and ether, and dried to produce 10 g of N-[5-(4-pyridinyl)-2-pyrimidinyl]acetamide, m.p. 261°–264° C.

B-6. N-[5-(4-Pyridinyl)-2-pyrimidinyl]-propanamide—A mixture containing 17 g of 5-(4-pyridinyl)-2-pyrimidinamine, 78 g of propionic anhydride and 500 ml of chloroform was refluxed for 90 minutes after which time no apparent reaction had taken place. To the reaction mixture was added 30 ml of pyridine and refluxing was continued for 4 hours, after which time no apparent reaction had taken place. The chloroform was then stripped off in vacuo, 200 ml of pyridine was added and the reaction mixture was refluxed for 40 hours and cooled. The separated solid was collected, washed with ethyl acetate and dried. The filtrate was stripped in vacuo and the resulting residue was treated with cold water, collected, washed with a small quantity of water and dried. The solids were combined, recrystallized from dimethylformamide, washed successively with ethanol and ether and dried to produce 9.5 g of N-[5(4-pyridinyl)-2-pyrimidinyl]-propanamide, m.p. 220°223° C.

Acid-addition salts of N-[5-(4-pyridinyl)-2-pyrimidinyl]propanamide are conveniently prepared by adding to a mixture of 1 g of N-[5-(4-pyridinyl)-2-pyrimidinyl]-propanamide in about 20 ml of aqueous methanol the appropriate acid, e.g., methanesulfonic acid, concentrated sulfuric acid, concentrated phosphoric acid, to a pH of about 2 to 3, chilling the mixture after partial evaporation and collecting the precipitated salt, e.g., dimethanesulfonate, sulfate, phosphate, respectively. Also, the acid-addition salt is conveniently prepared in aqueous solution by adding to water with stirring molar equivalent quantities each of N-[5-(4-pyridinyl)-2-pyrimidinyl]-propanamide and the appropriate acid, e.g., lactic acid or hydrochloric acid, to prepare respectively the lactate or hydrochloride salt of N-[5-(4-pyridinyl)-2-pyrimidinyl]-propanamide in aqueous solution.

Following the procedure of Example B-1 or B-2 using in place of 3-dimethylamino-2-(4-pyridinyl)-2-propen-1-al or 3-dimethylamino-2-(4-pyridinyl)-2-propen-1-al and 1,1-dimethylguanidine sulfate or guanidine carbonate molar equivalent quantities of the appropriate 3-dimethylamino-3-Q'-2-PY-2-propen-1-al and guanidine derivative, it is contemplated that the corresponding compounds of Examples B-7 through B-11 can be obtained.

B-7. 5-(3-Pyridinyl)-2-pyrimidinamine, using 3-dimethylamino-2-(3-pyridinyl)-2-propen-1-al and guanidine carbonate.

B-8. 5-(2-Methyl-3-pyridinyl)-2-pyrimidinamine, using 3-dimethylamino-2-(2-methyl-3-pyridinyl)-2-propen-1-al and guanidine carbonate.

B-9. 5-(2-Methyl-4-pyridinyl)-2-pyrimidinamine, using 3-dimethylamino-2-(2-methyl-4-pyridinyl)-2-propen-1-al and guanidine sulfate.

B-10. 4-Methyl-5-(5-methyl-3-pyridinyl)-2-pyrimidinamine, using 3-dimethylamino-3-methyl-2-(5-methyl-3-pyridinyl)-2-propen-1-al and guanidine sulfate.

B-11. N,N-Dimethyl-5-(2,6-dimethyl-4-pyridinyl)-2-pyrimidinamine, using 3-dimethylamino-2-(2,6-dimethyl-4-pyridinyl)-2-propen-1-al and 1,1-dimethylguanidine sulfate.

The usefulness of the compounds of formulas I and II, or pharmaceutically acceptable acid-addition salts thereof, as cardiotonic agents is demonstrated by their effectiveness in standard pharmacological test procedures, for example, in causing a significant increase in the contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1978.

When tested by the isolated cat or guinea pig atria and papillary muscle procedure, the compounds of formulas I and II, or pharmaceutically acceptable acid-addition salts thereof at doses of 10, 30, 100 and/or 300 μg/ml, were found to cause significant increases, that is, greater than 25% (cat) or 30% (guinea pig) in papillary muscle force and significant increases, that is, greater than 25% (cat) or 30% (guinea pig), in right atrial force, while causing a lower percentage increase in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, when tested at one or more said dose levels by this procedure in the cat or guinea pig test, the compounds of the invention were found to cause respective increases in papillary muscle force (PMF) and right atrial force (RAF) given in Table A.

TABLE A

| Example | Cat or g.p. | Dose μg/ml | In Vitro Cardiotonic Activity Percentage Increase | | | |
|---------|-------------|------------|---------|---------|---------|---------|
|         |             |            | RAR[a]  | RAF[b]  | PMF[c]  | N[d]    |
| A-1     | cat         | 100        | 48      | 57      | 104     | 3/4     |
| A-2     | cat         | 30         | 20      | 26      | 38      | 3/5     |
|         |             | 100        | 44      | 51      | 66      | 3/5     |
| A-3     | g.p.        | 30         | 10      | 32      | 56      | 6/8     |
|         |             | 100        | 19      | 118     | 127     | 6/8     |
| A-4     | cat         | 30         | 30      | 34      | 63      | 3/5     |
|         |             | 100        | 30      | 107     | 179     | 3/5     |
| A-5     | g.p.        | 100        | 0       | 36      | 68      | 3/4     |
| B-1     | cat         | 30         | 8       | 26      | 26      | 2/3     |
|         |             | 100        | 12      | 40      | 79      | 2/3     |
| B-2     | g.p.        | 100        | 41      | 279     | 51      | 3/5     |
| B-3     | cat         | 100        | 33      | 57      | 63      | 2/2     |
| B-4     | g.p.        | 10         | 20      | 50      | 84      | 3/5     |

TABLE A-continued

| Example | Cat or g.p. | Dose μg/ml | In Vitro Cardiotonic Activity Percentage Increase | | | |
|---|---|---|---|---|---|---|
| | | | RAR[a] | RAF[b] | PMF[c] | N[d] |
| | | 30 | 49 | 96 | 147 | 3/5 |
| | | 100 | 60 | 191 | 198 | 3/5 |
| B-5 | cat | 100 | 15 | 31 | 54 | 2/5 |
| B-6 | cat | 300 | 15 | 58 | 36 | 2/2 |

[a]Right atrial rate.
[b]Right atrial force.
[c]Papillary muscle force.
[d]Number of preparations.

When tested by said anesthetized dog procedure, the compounds of formula I or II at doses of 3.0 and/or 10.0 mg/kg administered intravenously were found to cause significant increases, that is, 25% or greater, in cardiac contractile force or cardiac contractility with lower changes in heart rate and blood pressure. For example, when tested at one or more of said dose levels by this procedure, the compounds of Examples B-2, B-5 and B-6 were found to cause increases of about 30% to 90% in contractile force and lower changes in heart rate and blood pressure.

The present invention includes within its scope a cardiotonic composition comprising a pharmaceutically acceptable carrier and, as the active component thereof, the cardiotonic compound of formula I or II or pharmaceutically acceptable acid-addition salt thereof. The invention also includes within its scope the method for increasing cardiac contractility in a patient requiring such treatment which comprises administering to such patient a cardiotonically effective amount of the compound of formula I or II or pharmaceutically acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc, and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic ester such as ethyl oleate. These compositions can also contain adjuvants such as stabilizing, preserving, wetting, emulsifying and dispersing agents.

They can be sterilized, for example by filtration through a bacterial-retaining filter, by incorporation of sterilizing agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied to that a suitable dosage is obtained. The dosage administered to a particular patient is variable, depending upon the clinician's judgement using as the criteria: the route of administration, the duration of treatment, the size and condition of the patient, the potency of the active component of the patient's response thereto. An effective dosage amount of active component can thus only be determined by the clinician considering all criteria and utilizing his best judgement on the patient's behalf.

We claim:

1. A 4-PY-5-Q-2-pyrimidinamine or 5-PY-4-Q'-2-pyrimidinamine having the formula

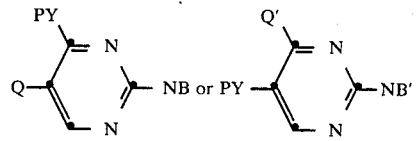

or acid-addition salt thereof, where PY is 4- or 3-pyridinyl or 4- or 3-pyridinyl having one or two lower-alkyl substituents, Q and Q' are each hydrogen or methyl, NB is dimethylamino or N-(2-hydroxyethyl)methylamino and NB' is amino or dimethylamino.

2. A compound according to claim 1 where PY is 4-pyridinyl or 3-pyridinyl and Q is hydrogen.

3. A 4-PY-5-Q-2-pyrimidinamine according to claim 1 where PY is 4-pyridinyl, Q is hydrogen and NB is dimethylamino.

4. A 4-PY-5-Q-2-pyrimidinamine according to claim 1 where PY is 3-pyridinyl, Q is hydrogen and NB is dimethylamino.

5. A 4-PY-5-Q-2-pyrimidinamine according to claim 1 where PY is 3-pyridinyl, Q is hydrogen and NB is N-(2-hydroxyethyl)methylamino.

6. A 5-PY-4-Q'-2-pyrimidinamine according to claim 1 where PY is 4-pyridinyl, Q' is methyl and NB' is amino.

7. A cardiotonic composition for increasing cardiac contractility, said composition comprising a pharmaceutically acceptable inert carrier and, as the active component thereof, a cardiotonically effective amount of 4-PY-5-Q-2-pyrimidinamine or 5-PY-4-Q'-2-pyrimidinamine according to claim 1 or pharmaceutically acceptable acid-addition salt thereof where PY is 4- or 3-pyridinyl or 4- or 3-pyridinyl having one or two lower-alkyl substituents, Q and Q' are each hydrogen or methyl, NB is dimethylamino or N-(2-hydroxyethyl)methylamino and NB' is amino or dimethylamino.

8. The method for increasing cardiac contractility in a patient requiring such treatment which comprises administering orally or parenterally in a solid or liquid dosage form to such patient a cardiotonically effective amount of 4-PY-5-Q-2-pyrimidinamine or 5-PY-4-Q'-2-pyrimidinamine according to claim 1 or pharmaceutically acceptable acid-addition salt thereof, where PY is 4- or 3-pyridinyl or 4- or 3-pyridinyl having one or two lower-alkyl substituents, Q and Q' are each hydrogen or methyl, NB is dimethylamino or N-(2-hydroxyethyl)methylamino and NB' is amino or dimethylamino.

* * * * *